United States Patent
Law et al.

(10) Patent No.: US 7,254,445 B2
(45) Date of Patent: *Aug. 7, 2007

(54) MULTIPROGRAMMABLE TISSUE STIMULATOR AND METHOD

(75) Inventors: Jay Law, Denver, CO (US); William Borkan, North Miami Beach, FL (US); Lance Ehren, Dallas, TX (US); George Van Campen, Fort Lauderdale, FL (US); John Erickson, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 338 days.

This patent is subject to a terminal disclaimer.

(21) Appl. No.: 10/901,900

(22) Filed: Jul. 28, 2004

(65) Prior Publication Data

US 2005/0090876 A1    Apr. 28, 2005

Related U.S. Application Data

(63) Continuation of application No. 10/444,250, filed on May 23, 2003, now Pat. No. 7,127,297, which is a continuation of application No. 08/659,919, filed on Jun. 7, 1996, now Pat. No. 6,609,031.

(51) Int. Cl.
*A61N 1/34* (2006.01)
(52) U.S. Cl. .................. 607/46; 607/59; 607/2
(58) Field of Classification Search .............. 607/59, 607/30, 2, 7, 11, 46, 60, 66, 68, 70, 73
See application file for complete search history.

(56) References Cited

U.S. PATENT DOCUMENTS

| 3,646,940 A | 3/1972 | Timm et al. ............. 128/421 |
| 3,724,467 A | 4/1973 | Avery et al. ............ 128/418 |
| 3,822,708 A | 7/1974 | Zilber .................... 128/419 R |
| 3,888,261 A | 6/1975 | Maurer | |

(Continued)

FOREIGN PATENT DOCUMENTS

EP    0 624 383    11/1994

(Continued)

OTHER PUBLICATIONS

Neurostimulation, An Overview; Lazorthes, et al.; Futura Publishing Company, Inc.; 20 pages, 1985.

(Continued)

*Primary Examiner*—Kennedy Schaetzle
(74) *Attorney, Agent, or Firm*—Peter R. Lando; Christopher S. L. Crawford

(57) ABSTRACT

An electronic stimulation system is used to control pain over multiple regions of a patient's body. The system has one or more percutaneous leads, each having multiple electrodes, implanted within the patient's epidural space parallel to the axis of the spinal cord. The leads are connected to either a totally implanted system or a radio frequency system. The system is able to treat pain over different regions of a patient's body by "simultaneously" stimulating the patient with at least three different stimulation settings. "Simultaneous" stimulation involves sequentially stimulating the patient with the multiple stimulation settings such that the patient receives the cumulative effect of each stimulation setting, while not perceiving the transition from one stimulation setting to another.

10 Claims, 3 Drawing Sheets

U.S. PATENT DOCUMENTS

| | | | |
|---|---|---|---|
| 3,920,025 A | 11/1975 | Stasz et al. | |
| 4,019,518 A | 4/1977 | Maurer et al. | |
| 4,026,301 A | 5/1977 | Friedman et al. | |
| 4,167,190 A | 9/1979 | Sorenson et al. | |
| 4,230,121 A | 10/1980 | Stanton | |
| 4,232,679 A | 11/1980 | Schulman | 128/419 PG |
| 4,338,945 A | 7/1982 | Kosugi et al. | 128/421 |
| 4,365,633 A | 12/1982 | Loughman et al. | |
| 4,379,462 A | 4/1983 | Borkan et al. | |
| 4,390,023 A | 6/1983 | Rise | |
| 4,398,537 A | 8/1983 | Holmbo | |
| 4,424,812 A | 1/1984 | Lesnick | 128/419 PG |
| 4,459,989 A | 7/1984 | Borkan | |
| 4,539,993 A | 9/1985 | Stanton | |
| 4,612,934 A | 9/1986 | Borkan | |
| 4,688,574 A | 8/1987 | Dufresne et al. | |
| 4,690,144 A | 9/1987 | Rise et al. | |
| 4,735,204 A | 4/1988 | Sussman et al. | 128/419 R |
| 4,744,371 A | 5/1988 | Harris | |
| 4,793,353 A | 12/1988 | Borkan | |
| 4,958,632 A | 9/1990 | Duggan | 128/419 PG |
| 5,031,618 A | 7/1991 | Mullett | |
| 5,058,584 A | 10/1991 | Bourgeois | |
| 5,119,832 A | 6/1992 | Xavier | |
| 5,121,754 A | 6/1992 | Mullett | |
| 5,193,538 A * | 3/1993 | Ekwall | 607/29 |
| 5,207,218 A | 5/1993 | Carpentier et al. | |
| 5,251,634 A | 10/1993 | Weinberg | |
| 5,342,409 A | 8/1994 | Mullett | |
| 5,370,672 A | 12/1994 | Fowler et al. | |
| 5,374,285 A | 12/1994 | Vaiani et al. | |
| 5,397,338 A | 3/1995 | Grey et al. | |
| 5,413,592 A | 5/1995 | Schroeppel | |
| 5,417,719 A | 5/1995 | Hull et al. | |
| 5,423,877 A | 6/1995 | Mackey | |
| 5,425,364 A | 6/1995 | Imran | |
| 5,433,736 A | 7/1995 | Nilsson | 607/59 |
| 5,443,486 A * | 8/1995 | Hrdlicka et al. | 607/59 |
| 5,456,254 A | 10/1995 | Pietroski et al. | |
| 5,458,631 A | 10/1995 | Xavier | |
| 5,462,545 A | 10/1995 | Wang et al. | |
| 5,501,703 A | 3/1996 | Holsheimer et al. | 407/46 |
| 5,540,727 A | 7/1996 | Tockman et al. | |
| 5,562,718 A | 10/1996 | Palermo | |
| 5,626,629 A | 5/1997 | Faltys et al. | 607/57 |
| 5,713,937 A | 2/1998 | Nappholz et al. | 607/30 |
| 5,716,382 A | 2/1998 | Snell | |
| 6,249,703 B1 | 6/2001 | Stanton et al. | 607/30 |
| 6,609,031 B1 * | 8/2003 | Law et al. | 607/46 |

FOREIGN PATENT DOCUMENTS

| | | |
|---|---|---|
| EP | 0 532 143 | 3/1997 |

OTHER PUBLICATIONS

Medtronic; Itrel 3 System; Physician and Hospital Staff Manual; Medtronic B.V.; 21 pages, Nov. 1994.

Medtronic; Itrel 3; Patient Manual; Medtronic B.V.; 19 pages, Jun. 1994.

Programalith Series; Programmable-Interrogatable Pacing Systems; Physician's Manual; Pacesetter Systems, Inc.; 25 pages, 1981.

Pacesetter; Synchrony 2020T Rate-Modulated Polarity Programmable Dual-Chamber Pacemaker; DDDR; Technical Manual; Pacesetter Systems, Inc.; 31 pages, 1988.

"Computer-Controlled Spinal Cord Stimulation Shown Superior to Conventional Programming", Anesthesiology News, Jun. 1996.

"The role of Spinal Cord Stimulation in Contemporary of Pain Management", APS Journal 2(2), pp. 91-99, 1993.

"Patient-Interactive, Computer-Controlled Neurological Stimulation System: Clinical Efficacy in Spinal Cord Stimulator Adjustment", Neurosurg., vol. 76, Jun. 1992, North, Richard B.: "Spinal Cord Stimulation for Chronic, Intractable Pain", Electrical and Magnetic Stimulation of the Brain and Spinal Cord, Copyright 1993, Chapter 25, pp. 289-301.

"Spinal Cord Stimulation For Chronic, Intractable Pain: Experience Over Two Decades", Neurosurgery, vol. 32, No. 3, Mar. 1993.

"Spinal Cord Stimulation for Chronic Pain", Neurosurgery clinics of North America, vol. 6, No. 1, Jan. 1995.

Spinal Cord Stimulation for Chronic, Intractable Pain: Superiority of "Multi-Channel Devices" Pain, 44 (1991), pp. 119-130.

Neuromed, Inc., Physician Manual for Model MNT-916 Neurostimulator Transmitter, Neuromed. Inc., Sep. 1994.

"Patient-Interactive, Computer-Controlled Neurological Stimulation System: Clinical Efficacy in Spinal Cord Stimulator Adjustment", Neurosurg., vol. 76, Jun. 1992.

North, Richard B., "Spinal Cord Stimulation for Chronic, Intractable Pain", Electrical and Magnetic Stimulation of the Brain and Spinal Cord, Copyright 1993, Chapter 25, pp. 289-301.

* cited by examiner

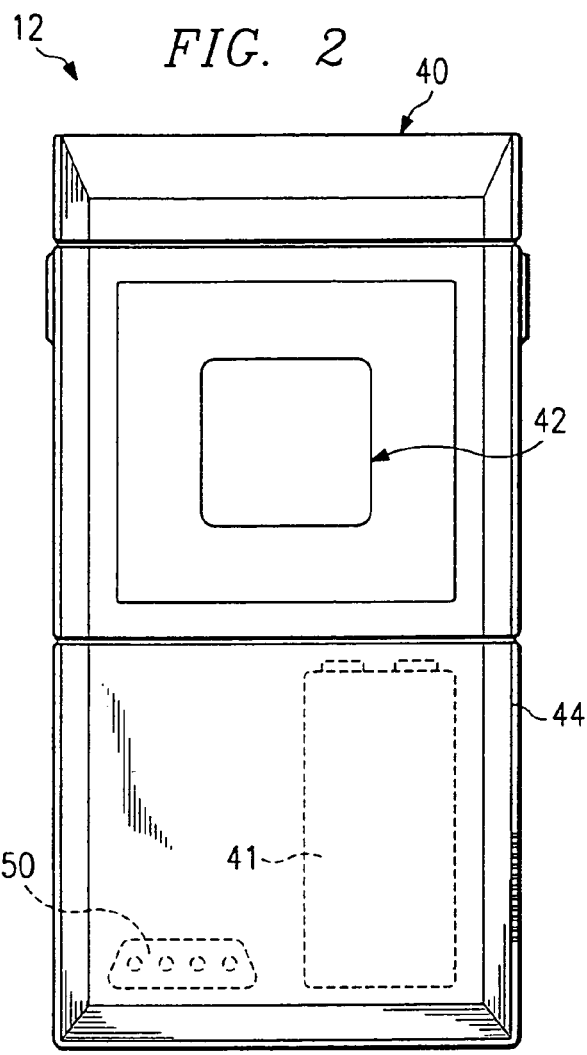
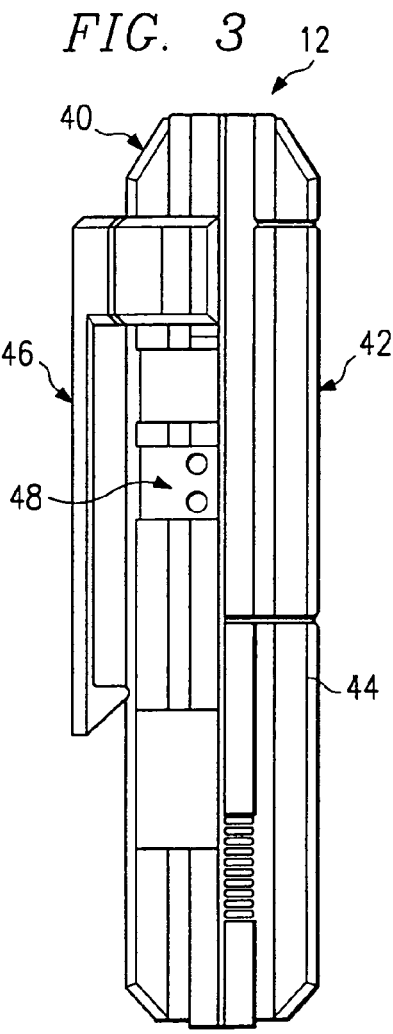
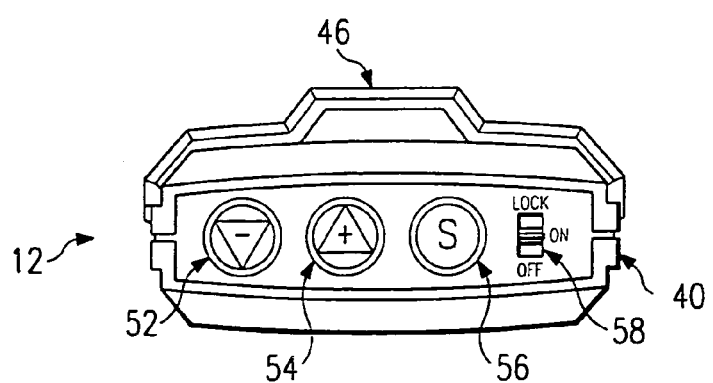

MULTIPROGRAMMABLE TISSUE STIMULATOR AND METHOD

CROSS-REFERENCE TO RELATED APPLICATIONS

This application is a continuation of prior application U.S. Ser. No. 10/444,250 filed May 23, 2003 now U.S. Pat. No. 7,127,297, which is a continuation of U.S. Ser. No. 08/659,919 filed on Jun. 7, 1996 (now U.S. Pat. No. 6,609,031), which are hereby incorporated by reference.

FIELD OF THE INVENTION

This invention relates to an electronic tissue stimulator. More specifically, the invention relates to an improved neuromodulation system for managing various diffuse and multi-focal neurological and/or motor disorders.

BACKGROUND OF THE INVENTION

The concept of using electronic stimulation systems to control pain by nerve or muscle stimulation is well known. Spinal cord stimulation (SCS) is a technique that has been used for pain management since the 1960s. SCS systems feature a pulse generator, discussed further below, coupled to one or more percutaneous leads having a plurality of electrodes (systems may also use a paddle-type lead that requires insertion by laminectomy). The leads are positioned within a patient's epidural space, parallel to the axis of the spinal cord. The leads' electrodes are used to deliver a particularized electric field to a specific region of the spinal cord or surrounding tissue. Applying an electric field across one or more nerve bundles and/or nerve roots can produce paresthesia, or a subjective sensation of numbness, tingling or "pins and needles," at the affected nerves' dermatomes. This paresthesia, if properly directed and produced at the necessary levels, can "mask" certain forms of chronic pain.

The focus, characteristics and intensity of the generated electric field are determined by the electrode configuration (i.e., the polarity, if any, assumed by each electrode) and the electric pulse waveform (collectively "stimulation setting"). The waveform properties include, at least, a stimulation frequency, a stimulation pulse width and phase information.

SCS systems are of two types. The most common system is a totally implanted pulse generator (IPG). An IPG consists of a surgically implanted, internally-powered pulse generator and, typically, a single multi-electrode lead. Once implanted, the IPG may be activated and controlled (programmed) by an outside telemetry source. The patient, being largely relieved of daily interaction with the system, uses a small magnet to both turn the system on and off, and limitedly control the stimulation settings. The internalized power source limits the life of these systems to between two and four years. After the power source is expended, the patient is required to undergo replacement surgery to continue electrical stimulation.

The second type of SCS system is a radio frequency (RF) system. An RF system consists of a surgically implanted, passive receiver and a transmitter which is worn externally. The transmitter is connected to an antenna which is positioned, externally, over the site of the implanted receiver. In operation, the transmitter communicates, through an RF signal, to the implanted receiver. Just as with the IPG system, electrical stimulation is delivered via implanted leads. Differing from an IPG, however, RF systems typically possess greater power resources, thereby enabling RF systems to utilize multiple leads. An RF system, like the one described herein, is disclosed in U.S. Pat. No. 4,612,934, issued Sep. 23, 1986 to Borkan.

Although existing systems have proven effective, these systems provide only qualified relief to patients who experience multi-focal or complex pain. Current SCS systems can address, at a maximum, two distinct pain patterns—a "pain pattern" being a dermatome, dermatome segment or series of dermatomes afflicted by pain. One current system features two percutaneous leads, wherein the user can elect to address up to two unilateral pain patterns or a single non-complex, non-migrating bilateral pain pattern.

"unilateral pain" is said to be that pain which is localized on one side of the patient's body or the other. Unilateral pain is most efficiently addressed through a "unilateral electrode array," or a lead which is positioned to one side or the other of the physiological midline of the spine, e.g., an electrode positioned to the left of the physiological midline typically addresses pain located on the left side of the patient's body. Therefore, logically, "bilateral pain" is that pain which affects both sides of the patient's body, for example, lower back pain is often considered bilateral in nature. A bilateral electrode array generates an electric field to address bilateral pain. A bilateral electrode array may take two forms: (i) a single multi-electrode array positioned on or immediately about the physiological midline of the patient; or (ii) two parallel multi-electrode leads positioned to either side of the physiological midline, in which the leads produce a single electric field which transverses the spinal cord. As began above, the system of this example can be configured to address two unilateral pain patterns or a single bilateral pain pattern. The limitation inherent with this system is that a patient can experience only "either-or" pain management. Therefore, the patient is restricted to the simplest form of "multi-focal" stimulation applications.

For those patients whose pain does not conform to the non-yielding stricture of prior art systems, it would be desirable to provide an improved SCS system, whether an IPG or RF system, which could accommodate three or more stimulation settings to address diffuse, multi-focal pain, whether of a unilateral or bilateral nature or any combination thereof. A further desire would be to allow a patient, at will, to tailor a stimulation treatment from a group of programmed stimulation settings, wherein the patient may select: (i) a single stimulation setting, (ii) any number of stimulation settings from the programmed group, the selected settings being administered "simultaneously" or (iii) "simultaneous" stimulation of all programmed stimulation settings. "Simultaneous" stimulation being a mode of operation wherein each selected stimulation setting is delivered to the patient, the patient receiving the cumulative effect of each stimulation setting, and not substantially perceiving the transition from one stimulation setting to another.

In addition to the use of this technology for pain management, some researchers believe that SCS may have beneficial application in obtaining relief from and/or controlling the physical effects of peripheral vascular disease (PVD), angina pectoris, and various motor disorders.

SUMMARY OF THE INVENTION

It is, therefore, an object of the invention to provide an improved SCS system, the improved system being capable of being programmed with three or more stimulation settings to generate a corresponding number of electrical stimulation pulses.

It is another object of the invention to provide an improved SCS system which allows a patient, at will, to tailor a stimulation treatment from a group of programmed stimulation settings, wherein the user may select: (i) a single stimulation setting, (ii) any number of stimulation settings from the programmed group, the selected settings being administered "simultaneously" or (iii) "simultaneous" stimulation of all programmed stimulation settings.

These and other objects of the invention are obtained by providing a microcomputer controlled system. The improved system is capable of storing and delivering at least three stimulation settings, each stimulation setting potentially addressing a differing region of the patient's body. As well, each stimulation setting can produce, if the system possesses more than one multi-electrode catheter, electric fields characteristic of either a unilateral or bilateral electrode array.

For example, for an RF system, the transmitter may store a plurality of stimulation settings. Stimulation settings include data concerning, at least, an electrode configuration (the defined electric polarity of each electrode, if any), a stimulation amplitude, a stimulation frequency, a stimulation pulse width and signal phase information. The treatment information is encoded in the transmitter and impressed on an RF carrier signal which is broadcast through a transmission antenna to the system's implanted receiver.

An RF transmitter embodying the present invention is configured to include three or more setting data registers. Each of these data registers can be programmed to store an independent stimulation setting. Each independent stimulation setting can potentially target distinct regions of the patient's body to relieve pain or address other conditions such as motor disorders. Associated with each of the different stimulation settings is a stimulation amplitude. Independent amplitude registers store each of the amplitude values. Since each amplitude is associated with a stimulation setting, this embodiment includes an equal number of setting data registers and amplitude registers. Each of the setting data registers are connected to a setting select multiplexer which is used to select a particular stimulation setting to be broadcast by the transmitter. Similarly, an amplitude select multiplexer is used to select the amplitude information associated with the selected stimulation setting.

To control the stimulation setting and associated amplitude broadcast to the receiver, the transmitter includes a programmable setting time generator which is controlled by the microcomputer. The setting time generator generates a treatment interval which is sent to a programmable setting counter. The treatment interval is the interval that a particular stimulation setting is broadcast before the transmitter switches to the next stimulation setting. In the "simultaneous" operations mode, the treatment modality is set such that the patient cannot discern the switching between stimulation setting intervals, or pulses, and feels only the cumulative effect of all settings. The setting counter uses the treatment interval to control the select lines of the setting and amplitude multiplexers. The counter allows the setting counter to cycle through the desired stimulation settings substantially sequentially and ensures that all elected settings are broadcast.

The system further includes a clock to provide a signal at a continuous frequency. This frequency is altered by a frequency divider according to the microcomputer, in accordance with the selected stimulation setting, to produce the desired stimulation frequency. The stimulation frequency is sent to a pulse width modulator which modifies the stimulation frequency to add the selected pulse width. All of the treatment information is combined at an RF modulator which impresses the combined treatment information on an RF carrier for broadcasting to the receiver.

The above embodiment is but one example and such example shall not be construed as limiting the scope of the present invention. In an alternative form, the present invention may be embodied in an IPG system. Other objects and advantages of the present invention will be apparent to those of ordinary skill in the art having reference to the following specification together with the drawings.

BRIEF DESCRIPTION OF THE DRAWINGS

Other objects and features of the invention will become more readily apparent from the following detailed description when read in conjunction with the accompanying drawings, wherein:

FIG. 2 is a frontal view of the transmitter used in the partially implanted electronic stimulation system;

FIG. 3 is a side view of the transmitter shown in FIG. 2;

FIG. 4 is a top view of the transmitter shown in FIG. 2; and

DETAILED DESCRIPTION

Figure 1:
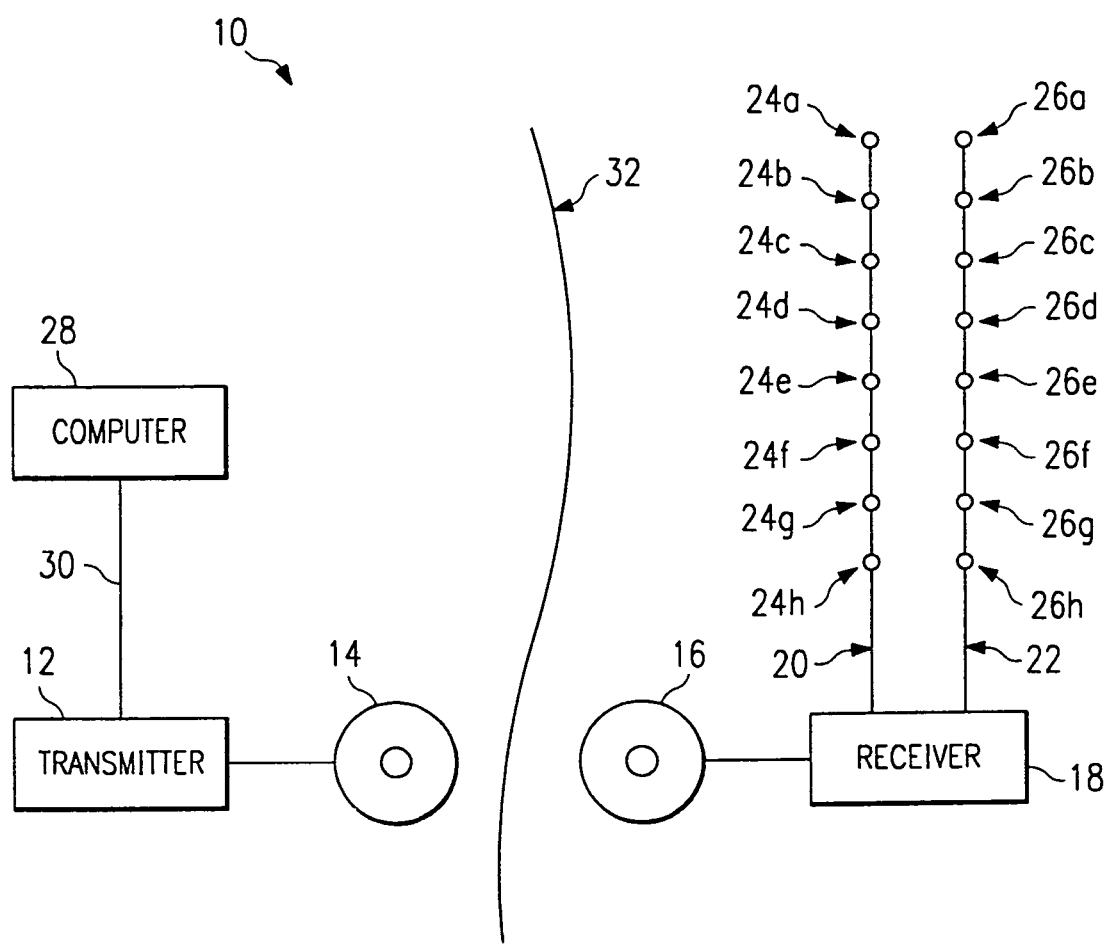
FIG. 1 is a functional block diagram of partially implanted electronic tissue stimulation system.

Referring now to the drawings, FIG. 1 illustrates a simplified block diagram of one embodiment of an electronic tissue stimulation system. The embodiment depicted is a radio frequency (RF) system and, particularly, a multi-channel neurostimulator having two multi-electrode catheters 20, 22. Stimulation system 10 essentially includes transmitter 12 and receiver 18. Receiver 18, including reception antenna 16, and multi-electrode catheters 20, 22 are surgically implanted beneath patient's skin 32. Transmitter 12 combines programmed stimulation settings with an RF carrier signal prior to passing the combination to the transmission antenna 14. From transmission antenna 14, the RF carrier signal/stimulation settings are transmitted through patient's skin 32 to reception antenna 16 and receiver 18.

The programmed stimulation settings specifically define and characterize the administered electric stimulation. In one embodiment, each stimulation setting is comprised of an electrode configuration and stimulation amplitude, stimulation frequency, stimulation pulse width and signal phase information. The electrode configuration defines whether each electrode is on or off and, if on, the polarity of such electrode. The amplitude is the intensity of the applied electric pulse. The frequency is the number of times the electrodes are turned on each second. The pulse width is the amount of time the electrodes are left on during each cycle. Finally, the signal phase setting defines the stimulation waveform as "monophasic" (either a positive or negative pulse) or "biphasic" (an alternating negative-positive or positive-negative pulse).

Receiver 18 demodulates the carrier signal and decodes the stimulation settings. Receiver 18 generates electrical pulses in accordance with the demodulated stimulation settings. The electrical pulses are realized at the distal ends of multi-electrode catheters 20, 22 through electrodes 24a-h and 26a-h. The generated electric pulses, assuming the characteristics of the active stimulation setting, may utilize any combination of unilateral or bilateral electrode arrays.

FIG. 2 is a frontal view of transmitter 12. Transmitter 12 includes case 40 which houses the electronics (not shown) and battery 41. Case 40 includes display 42 which preferably includes a liquid crystal display (LCD) as is well known in the art. Display 42 allows the electronics of transmitter 12 to display the current settings for the transmitter and to prompt a user for input via a menu driven series of informational display screens. Display 42 has backlighting capabilities, allowing display 42 to be viewable in dim lighting. To save power and increase battery life, the backlighting feature operates only briefly each time the user presses either plus key 54, minus key 52 or scroll/enter key 56. Access door 44 conceals an inner compartment that includes a 4-pin serial port connector 50 and a battery receptacle, for receiving a common alkaline battery 41 or other power source.

FIG. 3 illustrates a side view of transmitter 12. Clip 46 is removably coupled to case 40 to effectively secure transmitter 12 to a user's belt, pocket or the like. Antenna connector 48 connects transmitter 12 to antenna 14 (FIG. 1).

FIG. 4 is a top view of transmitter 12 and shows the user inputs which allow the user to interface with and program transmitter 12. Three position switch 58 allows the user to turn transmitter 12 off, or to place transmitter 12 in one of two operating states. When transmitter 12 is in the "on" position, the user may adjust the treatment information (i.e., stimulation settings) in transmitter 12 using the three input buttons 52, 54, 56 and display 42 as described below. However, when transmitter 12 is in the "lock" position, the user may review the treatment information on display 42, but cannot change any of the settings.

Scroll/enter key 56 allows each of the stimulation setting parameters (electrode configuration, amplitude, frequency, pulse width and phase) to be scrolled through, or called up sequentially, for programming. In this embodiment, scroll/enter key 56 also acts as an enter key when held down for at least two seconds. Plus key 54 and minus key 52 are used to adjust all parameter values by incrementing the parameter values up or down, respectively, when the specific parameter is displayed in display 42.

As an alternative to using transmitter controls 52, 54, 56, transmitter 12 may be connected to a specially programmed computer 28. Cable 30 (FIG. 1) electrically couples transmitter 12, through serial connection port 50, to computer 28. In addition to merely providing an alternative means for programming transmitter 12, computer 28 can enable data collection, stimulation setting optimization, electrode catheter placement feedback, and other functions associated with the pre-, intra-, and post-operative implantation of system 10. A specially programmed computer 28 could be the computer system described in the patent application, Ser. No. 08/659,874, filed Jun. 7, 1996, now U.S. Pat. No. 5,938,690, which is incorporated herein by reference.

It should be recognized that the present invention is not limited to RF systems. Rather, the present invention may also be implemented in the form of a totally implantable pulse generator (IPG). For an IPG, an external telemetry source would transmit programmable stimulation settings to the implanted component of the system.

Figure 5:
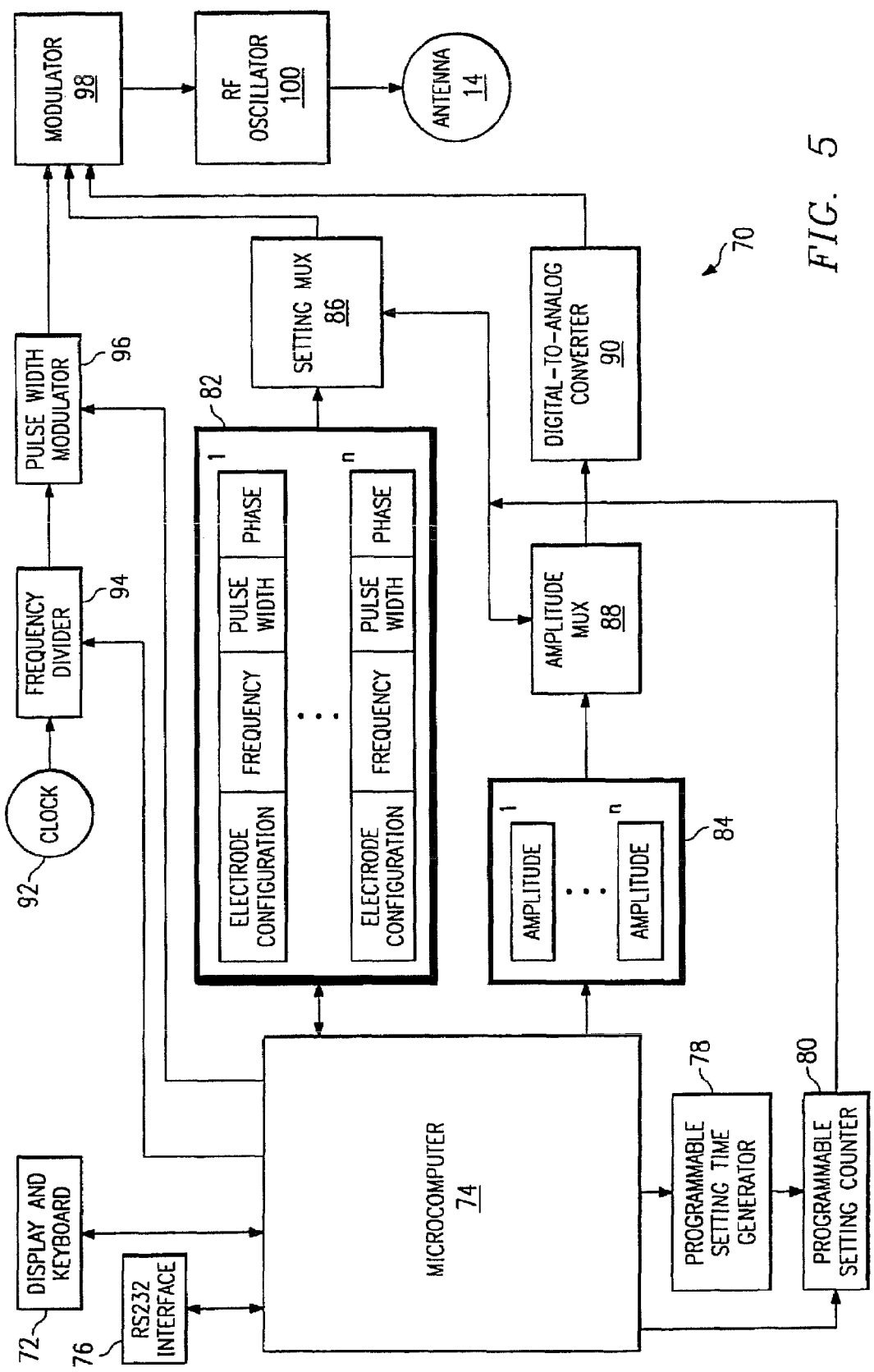
FIG. 5 is a functional block diagram of the circuit used to implement the transmitter used in the partially implanted electronic stimulation system.

FIG. 5 is a block diagram of the circuit used to implement the present invention. Circuit 70 includes microcomputer 74 which is used to control the various components of circuit 70.

A user interacts with system 10, and specifically microcomputer 74, through display and keyboard interface 72. For the RF system described above, display 42 and transmitter controls 52, 54, 56 collectively represent display and keyboard interface 72. For an IPG system, for example, a programmable telemetry source (not shown) provides a medium by which a user may communicate with the system 10.

Circuit 70 includes setting data registers 82. Each individual setting data register 82 stores information concerning electrode configuration(s), stimulation frequency, stimulation pulse width and signal phase. For a dual lead system, the stored electrode configuration will define a unilateral or bilateral electrode array. The preferred configuration of circuit 70 includes twenty-four individual setting data registers 82 to store up to twenty-four stimulation settings. Notwithstanding the preferred embodiment, one skilled in the art shall understand circuit 70 is not limited to the number of setting data registers shown by this specific embodiment. Further, setting data registers 82 can assume any form of memory, memory partitioning, or storage configuration to allow storage of stimulation setting data without departing from the scope of this invention.

Setting data registers 82 are individually connected to setting select multiplexer 86 which is used to select a particular simulation setting, excluding stimulation amplitude. The frequency and pulse width information are fetched by microcomputer 74 for operations that will be detailed below. The selected electrode configuration and phase information are sent to modulator 98 for combination with the setting's processed amplitude, frequency and pulse width information.

Amplitude registers 84 store the stimulation amplitudes associated with each of the stimulation settings stored in setting data registers 82. Accordingly, circuit 70 should be configured to include the same number of amplitude registers 84 as setting data registers 82 which, as stated above, is twenty-four in the preferred configuration. Amplitude select multiplexer 88 is used to select the amplitude corresponding to the selected stimulation setting. The selected amplitude is sent to digital-to-analog converter 90 where the digital amplitude information is converted into analog as required by modulator 98. One skilled in the art will understand that the amplitude registers 84 could be a part of the stimulation setting registers 82, or may assume some other storage configuration without departing from the scope of this invention.

Microcomputer 74 is connected to and controls setting time generator 78. Setting time generator 78 is programmable and used to implement a selected time interval provided by microcomputer 74 (based on the then active stimulation setting), which controls the amount of time an individual stimulation setting and amplitude are selected. For example, in the preferred embodiment, a stimulation setting runs for at least two pulses and shall not run less than 10 milliseconds. Alternatively, each pulse could represent a differing stimulation setting, with no significant time delay between each pulse. The selected time interval provided by setting time generator 78 is sent to setting counter 80. Setting counter 80 is programmable by microcomputer 74 and is used to select the proper stimulation settings and associated amplitudes corresponding to both a programmed sequence set, controlled by microcomputer 74, and to the time interval from the setting time generator 78. The count modulus of setting counter 80 is set by microcomputer 74 according to the number of individual stimulation settings to be used. Counter 80 is cycled such that each elected stimulation setting and amplitude is transmitted to receiver 18 (FIG. 1) for the time interval programmed into setting time generator 78. Time generator 78 and counter 80 accomplish the selection and switching by controlling the select line of setting select multiplexer 86 and amplitude select multiplexer 88, thereby controlling which stimulation setting and amplitude are sent and for how long each is sent to modulator 98.

Clock 92 is a standard oscillator which provides a known frequency to frequency divider 94. Frequency divider 94 modifies the signal from clock 92 according to the commands from microcomputer 74 to produce the desired treatment frequency. The desired treatment frequency is then sent from frequency divider 94 to pulse width modulator 96. Pulse width modulator 96 imposes the pulse width received from microcomputer 74 on the desired frequency. As stated earlier, the frequency of the treatment is the number of times the selected electrode combination is activated each second, while the pulse width of the treatment is the amount of time the electrode combination is on every time it is activated. The frequency and pulse width signal are sent from pulse width modulator 96 to modulator 98 where they are combined with (i) the electrode configuration and phase information from setting select multiplexer 86 and (ii) the analog amplitude information from digital-to-analog converter 90. In addition to combining this treatment information, modulator 98 encodes the combined treatment information on an RF carrier signal. The RF signal with the treatment information is sent from modulator 98 to RF oscillator 100. The output of oscillator 100 is delivered to antenna 14 where it is transmitted to receiver 18. As receiver 18 of this embodiment possesses no internalized power source, the transmission from antenna 14 includes that power necessary for receiver 18 to generate the defined electrical pulses.

Alternatively, receiver 18 may possess a plurality of registers similar to the configuration of FIG. 5. A receiver of this nature could assume the form of an IPG system or an RF system wherein the receiver 18 contains an internalized power source to maintain the content of the registers during non-transmission. The latter configuration would allow the reduction of the quantity of information transmitted between the transmitter 12 and receiver 18, thereby increasing the longevity of the transmitter power source.

In operation, microcomputer 74 can be programmed to administer any combination of stimulation settings. In a first mode, a user, through microcomputer 74, selects a single stimulation setting. The user may choose to deliver the single stimulation continuously or intermittently at a predefined or manually defined interval. In a second mode, the user, through microcomputer 74, selects any number of stimulation settings from a group of stored stimulation settings. As an example, user could select stimulation settings 1, 5, 7 and 12 of stimulation setting population 1-24. The selected stimulation settings are delivered for their respective time intervals in a continuous, substantially sequential manner. The period between each stimulation setting, if any, is minimal so that the patient substantially cannot detect the "transition" from one stimulation setting to the next, or at least do not find the change annoying. This stimulation technique allows the patient to perceive "simultaneous" stimulation in those regions subject to the stimulation settings. Moreover, stimulation of multiple regions may be accomplished with a minimal burden on system power resources. In a third mode, user selects all the stored stimulation settings. System 10 administers each stimulation setting in the same "simultaneous" approach as discussed above.

While the invention has been particularly shown and described with reference to a preferred embodiment, it will be understood by those skilled in the art that various changes in form and detail may be made therein without departing from the spirit and scope of the invention.

What is claimed is:

1. An implant device adapted to be implanted within a body of a patient, the implant device comprising:
    a plurality of setting data registers for storing a plurality of stimulation sets of parameters, wherein each stimulation set defines a respective electrode configuration and at least one pulse characteristic;
    circuitry for generating and delivering electrical pulses; and
    a controller for controlling the circuitry for generating and delivering, wherein, in at least one mode of operation, the controller controls the circuitry for generating and delivering to generate and deliver respective pulses according to the electrode configurations and pulse characteristics of at least three of the plurality of stimulation sets such that the patient perceives simultaneous stimulation at each site addressed by the at least three of the plurality of stimulation sets.

2. The implant device in accordance with claim 1 wherein each stimulation set comprises parameters defining an electrode configuration, a pulse width, and a pulse amplitude.

3. The implant device in accordance with claim 2 wherein each of the plurality of stimulation sets further comprises a parameter defining a pulse rate.

4. The implant device in accordance with claim 1 further comprising;
    wireless telemetry circuitry for receiving treatment selections, wherein the controller is responsive to the treatment selections to allow the patient to select any number of stimulation sets from the plurality stimulation sets for pulse generation operations.

5. A method of operating an implantable pulse generator to treat complex pain in a patient, the method comprising:
    storing a plurality of stimulation sets of parameters where each stimulation set defines a respective electrode configuration and at least one pulse characteristic, wherein each electrode configuration defines electrode polarities for electrodes implanted within the patient in at least two separate columns disposed bilaterally in an epidural space of the patient;
    receiving a treatment selection by the implantable pulse generator via wireless telemetry; and
    in response to the receiving, controlling pulse generating circuitry of the implantable pulse generator to generate and deliver respective pulses according to the electrode configurations and pulse characteristics of at least three of the plurality of stimulation sets such that the patient perceives simultaneous stimulation at each site addressed by the at least three of the plurality of stimulation sets.

6. The method of claim 5 wherein the treatment selection identifies a treatment protocol that treats a complex pain pattern comprising a bilateral pain pattern and a unilateral pain pattern.

7. The method of claim 5 wherein each stimulation set comprises parameters defining an electrode configuration, a pulse width, and a pulse amplitude.

8. The method of claim 7 wherein each stimulation set further comprises a parameter defining a pulse rate.

9. The method of claim 5 wherein the at least two separate columns are respectively disposed on two percutaneous leads implanted within the epidural space of the patient.

10. The method of claim 5 wherein the at least two separate columns are disposed on a paddle lead implanted within the epidural space of the patient.

* * * * *